United States Patent
Ishihara et al.

(10) Patent No.: US 7,338,774 B2
(45) Date of Patent: Mar. 4, 2008

(54) METHOD FOR DETERMINING ACTIVITY OF CELL CYCLE REGULATORY FACTOR AND METHOD FOR DIAGNOSING CANCER USING THE SAME

(75) Inventors: Hideki Ishihara, Hyogo (JP); Tomokazu Yoshida, Kobe (JP); Masatoshi Yamasaki, Kobe (JP); Sachiyo Tada, Osaka (JP)

(73) Assignee: Sysmex Corporation, Kobe-shi, Hyogo (JP)

( * ) Notice: Subject to any disclaimer, the term of this patent is extended or adjusted under 35 U.S.C. 154(b) by 750 days.

(21) Appl. No.: 10/074,041

(22) Filed: Feb. 14, 2002

(65) Prior Publication Data

US 2002/0164673 A1 Nov. 7, 2002

(30) Foreign Application Priority Data

Feb. 14, 2001 (JP) ............................. 2001-037115

(51) Int. Cl.
C12Q 1/48 (2006.01)
(52) U.S. Cl. ............................. 435/15; 435/4; 435/7.1
(58) Field of Classification Search ..................... 435/4, 435/183, 7.1, 28; 424/94.1
See application file for complete search history.

(56) References Cited

U.S. PATENT DOCUMENTS

| 4,252,783 | A | * | 2/1981 | Kam et al. | .................. | 436/501 |
| 4,529,313 | A | * | 7/1985 | Petermann et al. | ......... | 356/460 |
| 5,518,911 | A | * | 5/1996 | Abo et al. | .................. | 435/194 |
| 6,255,485 | B1 | * | 7/2001 | Gray et al. | ................. | 544/277 |

FOREIGN PATENT DOCUMENTS

| GB | 2 334 578 A | 8/1999 |
| WO | WO 98/02571 A1 | 1/1998 |
| WO | WO 99/29894 A1 | 6/1999 |

OTHER PUBLICATIONS

Pan et al., 1993, J Biol Chem, vol. 268:pp. 20443-20451.*
Hemmila, "Fluoroimmunoassays and immunofuorometric assays." 1985, Clin. Chem. vol. 31:pp. 359-370.*
Strachan and Read, Human Molecular Genetics 2, 1999, BIOS Scientific Publishers Ltd, Oxford, UK, Section 20.2.5., electronic version, pp. 1-9.*
Gopalakrishna et al (Analytical Biochemistry, 1992, 206:24-35).*
Pall Corporation ("PVDF membranes for Western Transfer and Sequencing", p. 1).*
Pan et al. (J Biol Chem, 1993, vol. 268: 20443-20451).*
Blain et al (Journal of Biological Chemistry, 1997, 272:25863-25872).*
Jeong and Nikiforv (BioTechniques, 1999, vol. 27: 1232-1238, IDS).*
Facemyer and Cremo (Bioconjug Chem, 1992, vol. 3: 408-413, IDS).*
Wataru Yasui, Sysmex Journal Web., p. 1 to p. 10, vol. 1, 2000.
Sang Jeong et al., BioTechniques, vol. 27, No. 6, pp. 1232-1237, Dec. 1999.
Chevaliers et al.; "Both cdc2 and cdk2 promote S phase initiation in Xenopus egg extracts"; Journal of Cell Science, vol. 108, No. 5, 1995; XP009055236; pp. 1831-1841.
Soos Timothy J. et al.; "Formation of p27-CDK Complexes during the Human Mitotic Cell Cycle"; Cell Growth and Differentiation, vol. 7, No. 2, 1996; XP009055234; pp. 135-146.
Kevin C. Facemyer et al.; Bioconjugate Chem.; vol. 3, No. 5, 1992, pp. 408-413.
Yumi Watanabe et al.; Brain Research, vol. 842, 1999, pp. 342-350.
Rita Derua et al.; Experimental Cell Research, vol. 230, No. 2, 1997, pp. 310-324.
Arata Shimada et al.; Biology of the Cell; vol. 90, No. 6-7, Oct. 1998, pp. 519-520.

* cited by examiner

*Primary Examiner*—Shanon Foley
*Assistant Examiner*—Laura B Goddard
(74) *Attorney, Agent, or Firm*—Birch, Stewart, Kolasch & Birch, LLP (57) ABSTRACT

A method for determining the activity of a cell cycle regulatory factor comprising the steps of:
    preparing a sample for measuring a cyclin-dependent kinase/cyclin complex from living cells;
    reacting adenosine 5'-O-(3-thiotriphosphate) (ATP-γS) with a substrate for the cyclin-dependent kinase in presence of the sample in order to introduce a monothiophosphate group into a serine or threonine residue of the substrate;
    labeling the substrate by coupling a labeling fluorophore or a labeling enzyme with a sulfur atom of the introduced monothiophosphate group;
    measuring the amount of fluorescence from the labeling fluorophore labeling the substrate, or reacting the labeling enzyme labeling the substrate with a substance which generates an optically detectable product by reaction with the labeling enzyme and optically measuring the amount of the generated product; and
    calculating the activity of the cyclin-dependent kinase from the measured amount of fluorescence or the measured amount of the generated product with reference to a pre-produced reference curve.

9 Claims, 4 Drawing Sheets

Sample 3
Sample 4
Sample 5

METHOD FOR DETERMINING ACTIVITY OF CELL CYCLE REGULATORY FACTOR AND METHOD FOR DIAGNOSING CANCER USING THE SAME

CROSS-REFERENCE TO RELATED APPLICATION

This application is related to Japanese Patent Application No. 2001-37115 filed on Feb. 14, 2001, whose priority is claimed under 35 USC § 119, the disclosure of which is incorporated by reference in its entirety.

BACKGROUND OF THE INVENTION

1. Field of the Invention

The present invention relates to a method for determining the activity of a cell cycle regulatory factor without using a radioisotope and a method for diagnosing a cancer using the method.

2. Description of Related Art

Cell proliferation is a fundamental and important feature of living things. The cell proliferation involves division of a single cell into two daughter cells, and somatic cells divide through a plurality of sequential reactions including growth of cells, replication of DNAs, distribution of chromosomes and division of cells. This chain of sequential reactions is referred to as a cell cycle. In the case of eucaryotic cells, the cell cycle is divided into four phases, that is, a synthetic (S) phase during which the replication of DNAs takes place, a mitotic (M) phase during which the division of cells takes place, a gap 1 (G1) phase which is an interphase from the M phase to the next S phase and a gap 2 (G2) phase which is an interphase from the S phase to the next M phase. In the G1 phase, cells receive a signal for proliferation, prepare for the replication of DNAs, and make metabolism and growth which are necessary for the division of cells. In the G2 phase, the cells prepare for the division. In the G1 phase, a transit point is experimentally assumed which is called an R point (restriction point) for mammalian cells and START for yeast. Typically, cells multiply in response to proliferation signals from the outside. The cells receive the signals in the G1 phase and progress the cell cycle. After passing through a certain point in the G1 phase, the cell cycle progresses from the S phase to the G2 phase, the M phase and then the G1 phase without stopping even if the proliferation signals are not received any longer. This certain point is the R point or START, and is a so-to-speak point at which the entering into cell cycle progression is determined. Further, the cells can leave the cell cycle and enter a resting (G0) phase during which the cell do not grow or multiply. Experimentally, the cells entering the resting phase, if given a suitable signal, can be returned to the G1 phase and induced to grow and divide again. It is considered that a lot of non-growing and non-multiplying cells of multicellular organisms are in the G0 phase.

There mainly exist two groups of cell cycle regulatory factors in cells. One is a group of kinases which are positive regulatory factors and are referred to as cyclin-dependent kinases (CDKs), and the other is a group of CDK inhibitors (CDKIs) which are negative regulatory factors. The CDKs exist in cytoplasm in the inactive form. The CDKs are activated, e.g., by phosphorylation, and move into nuclei in the cells. In the nuclei, the CDKs bind to cyclin molecules to form complexes with cyclin (referred to as activated CDKs hereinafter) and positively regulate the progress of the cell cycle at various steps of the cell cycle. On the other hand, the CDKIs inactivate the CDKs by binding to the activated CDKs or CDK simple substances, thereby regulating the cell cycle negatively.

There are now known seven types of CDKs, i.e., CDK1, CDK2, CDK3, CDK4, CDK5, CDK6 and CDK7 to which different cyclins are bound. More particularly, CDK1 binds to cyclin A or B, CDK2 binds to cyclin A or E, and CDK4 and CDK6 bind to cyclin D1, D2 or D3, to be activated. The activated CDKs control specific phases of the cell cycle. The following table 1 shows CDKs concerning the control of the cell cycle, cyclins which functionally bind to the CDKs, and phases of the cell cycle during which the activated CDKs act.

TABLE 1

| CDKs | Cyclins binding to CDKs | Phases of cell cycle in which activated CDKs act |
|---|---|---|
| CDK4, CDK6 | Cyclin D1, D2, D3 | G1 |
| CDK2 | Cyclin E | Transitional period from G1 to S |
| CDK2 | Cyclin A | S |
| CDK1 | Cyclin A, B | Transitional period from S to M, M |

Thus the cell cycle is controlled and the cell proliferation is regulated by activation of different types of CDKs. The activated CDKs are enzymes which phosphorylate serine residue and threonine residue in a protein as a substrate. In an in-vitro reaction system, the activated CDK1 and CDK2 react well on histone H1 as a substrate and the activated CDK 4 and CDK6 react well on Rb (retinoblastoma protein) as a substrate. In an in-vivo cell cycle regulation, it is considered that the activated CDKs require Rb as a physiologic substrate, but it is not known what other proteins act as substrates.

As described above, the CDKs and cyclins regulate the cell cycle in close association with each other. The multiplication of cyclin D1 gene is observed in a great number of cases of esophageal cancer, while over expression of cyclin D1 gene is observed in a great number of cases of stomach cancer and colon cancer. On the other hand, the multiplication of cyclin E gene is observed in stomach cancer and colon cancer but is not observed in esophageal cancer. Excessive expression of cyclin E in stomach and large bowel takes place with great frequency in cases of adenoma and adenocarcinoma and shows a significant correlation with malignancy such as invasion, progress of stages, metastasis and the like. The expression and kinase activity of CDK1 are remarkably accelerated in most cases of stomach cancer and colon cancer as compared with normal mucosal tissue. It is known that augmented expression of cyclin genes correlates with the progress and malignancy of various cancers (see Wataru Yasui, Sysmex Journal Web., p. 1 to p. 10, vol. 1, 2000).

Therefore, it is expected that measuring the activity of the individual species of CDKs will provide good indices of the type and malignancy of diseases related to the control of the cell cycle. In other words, generally at the R point, the expression of CDK2 decreases and the cell cycle arrest and the division of cells is controlled. However, if the expression of CDK2 increases at the R point, it means that the cell cycle fails to stop, i.e., it means a state of a disease such as cancer. If the expression of CDK4 or CDK6 increases, stomach cancer or colon cancer may be expected because stomach cancer and colon cancer involve accelerated gene expression of the cyclin D1 which bind specifically to CDK4 or CDK6. Thus, it is considered to be possible to determine the type of cancer.

Usually, the activity of the CDKs is determined using radioisotopes. More particularly, in the presence of a CDK which is extracted from a cell lysate by an immunoprecipitation method using an anti-CDK antibody and whose activity is unknown, $^{32}$P-labelled adenosine 5'-O-(3-triphosphate) (ATP) is reacted with serine residue or threonine residue in a substrate to introduce monophosphate group derived from the $^{32}$P-labelled ATP. The amount of $^{32}$P taken by the substrate is detected by autoradiography or by a scintillation counter. Thereby the amount of the phosphorylated substrate is measured and the activity of the CDK is calculated from the amount of the phosphorylated substrate.

This method requires careful attention in handling the substance and in disposal of waste liquid since it uses $^{32}$P which is a radioisotope.

SUMMARY OF THE INVENTION

Accordingly, are desired a method for measuring cell cycle regulatory factors accurately without using radioisotopes and a method for diagnosing cancer on the basis of measurement results.

The present invention is to provide a method for determining the activity of a cell cycle regulatory factor comprising the steps of:

preparing a sample for measuring a cyclin-dependent kinase/cyclin complex from cells;

reacting adenosine 5'-O-(3-thiotriphosphate) (ATP-γS) with a substrate for the cyclin-dependent kinase in presence of the sample in order to introduce a monothiophosphate group into a serine or threonine residue of the substrate;

labeling the substrate by coulping a labeling fluorophore or a labeling enzyme with a sulfur atom of the introduced monothiophosphate group;

measuring the amount of fluorescence from the labeling fluorophore labeling the substrate, or reacting the labeling enzyme labeling the substrate with a substance which generates an optically detectable product by reaction with the labeling enzyme and optically measuring the amount of the generated product; and calculating the activity of the cyclin-dependent kinase from the measured amount of fluorescence or the measured amount of the generated product with reference to a pre-produced reference curve.

Further, the present invention is to provide a method of diagnosing a cancer based on a result obtained by determination.

These and other objects of the present application will become more readily apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

For carrying out the method of the present invention, a sample is first prepared.

In the present invention, the sample which contains a cyclin-dependent kinase (CDK)/cyclin complex may contain a single type or plural types of CDK/cyclin complexes, but may preferably contain a single type of CDK/cyclin complex.

The sample which contains a CDK/cyclin complex (referred to as an activated CDK hereinafter) and is used in the method of the present invention is prepared by solubilizing cells and separating a sample containing the activated CDK to be determined from a liquid containing the solubilized cells.

CDKs usable in the present invention include CDK1, CDK2, CDK3, CDK4, CDK5, CDK6 and CDK7.

(1) Step of Solubilizing Cells

The sample is prepared from cells derived from animals including human beings such as a tissue sample (e.g., a biopsy sample, a surgically resected sample, etc.). The sample is to be tested as to whether or not it contains a CDK/cyclin complex as well as its activity. Since simple CDKs exist in cytoplasm and turn into activated CDKs by binding to cyclins in nuclei, cells need to be solubilized to extract the activated CDKs.

Accordingly, the cells are first solubilized by chemically or physically destroying the cell membranes and nuclear envelopes thereof. More particularly, the cells are preferably pulverized using a Waring blender, sucked and discharged using a syringe or ultrasonicated in a buffer containing a surfactant, a protease inhibitor and a phosphatase inhibitor, for example.

The surfactant is used for destroying cell membranes and nuclear envelopes so that intracellular substances can be taken out. However, the surfactant should have such a surface active property that the activated CDK is not decomposed. Examples thereof include Nonidet P-40, Triton X-100, deoxycholic acid and CHAPS. The concentration of the surfactant is preferably 1 w/v % or less.

The protease inhibitor is used for preventing the CDK and cyclin molecule, which are proteins, from being destroyed when mixed with intracellular substances when the cell membranes and nuclear envelopes are destroyed. Examples thereof include a mixture of a metalloprotease inhibitor such as EDTA, EGTA, etc., a serine protease inhibitor such as PMSF, trypsin inhibitor, chymotrypsin, etc., and/or a cysteine protease inhibitor such as iodoacetamide, E-64, etc., and a protease inhibitor cocktail commercially available from Sigma which contains such protease inhibitors premixed.

The phosphotase inhibitor is used for preventing the activated CDK, which is a protein itself, from changing its activity by hydrolysis of its phosphate group. Examples thereof include a serine/threonine phosphotase inhibitor such as sodium fluoride and a tyrosine phosphotase inhibitor such as sodium orthovanadate (Na$_3$VO$_4$).

After the cells are solubilized, insoluble matters are removed from cell lysate by centrifugation or by filtration using a filter. Subsequently, prior to separating the sample containing the activated CDK, it is preferable to measure the total amount of proteins in the cell lysate according to a method known to those skilled in the art. For example, the total amount of proteins may be measured using a DC protein kit using bovine IgG as a reference.

(2) Separation of Sample Containing Activated CDK to be Determined

The sample containing the activated CDK whose activity is to be determined is prepared from the thus obtained cell lysate. The sample containing the activated CDK can be prepared, for example, by an immunoprecipitation method.

According to the immunoprecipitation method, is used an anti-CDK antibody having a specificity to one of the CDKs 1 to 7 to be determined.

More particularly, the cell lysate containing a specific amount of protein is reacted with an anti-CDK antibody corresponding to the activated CDK to be determined and a suspension of sepharose beads (a beads content of 4 to 6 v/v %) coated with Protein A, Protein G or anti-rabbit IgG antibody as material for catching the anti-CDK antibody at 0 to 10° C. for one to two hours. Since these beads are insoluble, the complex of the anti-CDK antibody and the CDK bound to the beads become insoluble and precipitate.

By immunoprecipitation, all CDK family (including the simple CDK, the activated CDK, the complex of the activated CDK and CDKI and the complex of the CDK and CDKI) in the liquid containing solubilized cells are caught. Accordingly, the activated CDK are contained together with the simple CDK, the complex of the activated CDK and CDKI and the complex of CDK and CDKI in the prepared sample. However, the inactivated CDK does not involve monothiophosphorylation of the substrate in the presence of ATP-γS. If the present invention is carried out on a sample containing the inactivated CDK for determining the activity of the activated CDK, the activity of the inactivated CDK is not detected and only the activity of the activated CDK is determined.

Subsequently, the precipitated beads to which the complex of the activated CDK and the anti-CDK antibody are bound are washed. A buffer solution for washing the beads contains magnesium chloride since the activated CDK needs to form a complex with magnesium in order that ATP-γS acts on the substrate and the activated CDK later. The buffer solution also contains, for example, dithiothreitol (DTT) as a stabilizer necessary for stabilizing the molecular structure of the substrate. Further the buffer solution may contain albumin, a trace of a surfactant and/or the like.

Thereafter, the activity of the activated CDK in the sample is determined. The method of the present invention includes monothiophosphorylating the serine or threonine residue of the substrate in the presence of the activated CDK, labeling the resulting thiophosphorate group and measuring the label. In the present invention, the activated CDK bound to the CDK antibody caught by the beads may be used as an activated CDK.

(i) In the Presence of the Activated CDK, a Substrate, which is a Substrate for the CDK, is Reacted with Adenosine 5'-O-(3-thiotriphosphate) (ATP-γS) to Introduce a Monothiophosphate Group Derived from ATP-γS into the Serine Group and Threonine Group of the Substrate Usually, activated CDKs act to react ATP with the serine or threonine group of the substrate to introduce a monophosphate group derived from ATP. However, in the present invention, ATP-γS is used instead of ATP to introduce the monothiophosphate group instead of the monophosphate group in the serine or threonine group of the substrate.

For monothiophosphorylation, a liquid of pH 6.5 to 8.5, preferably 7.4, containing 0.1 to 1.0 mg/mL of the substrate is reacted with 10 to 100 equivalents of ATP-γS with respect to 1 equivalent of the substrate in the presence of the activated CDK at 25 to 40° C., preferably 37° C., for 5 minutes to 1 hour, preferably 10 minutes.

As discussed above, the sample contains not only the activated CDK but also the inactivated CDK. However, since only the activated CDK catalyzes the thiophosphate group introduction reaction, the inactivated CDK does not participate in the method of the present invention.

As examples of the substrate, histone H1 and Rb (Retinoblastoma protein) may be mentioned for the activated CDK1 and CDK2 and for the activated CD4 and CDK6, respectively.

In the present invention, regarding substrates such as Rb which essentially contain the cysteine residue in their molecules, the residue is substituted by an amino acid residue such as alanine which does not contain thiol group. This is for avoiding measurement errors owing to the labeling of the thiol group of the cysteine residue essentially present in the substrate at the same time when sulfur atom of thiophosphate group of the substrate (into which thiophosphate group derived from ATP-γS by the action of the activated CDK) is labeled with the labeling fluorophore or the labeling enzyme.

Regarding a substrate which essentially contains the cysteine residue in its molecules, it may be possible to produce, from the substrate, a substrate of which the cysteine residue is substituted by an amino acid residue such as alanine which does not contain the thiol residue, by PCR or by modifying a gene of the substrate by site mutagenesis and expressing the modified gene. Particularly, with regard to a substrate such as Rb which contains the cysteine residue, a recombinant vector is obtained by cloning with use of oligonucleotide primers Rb-1 (5'-ACA GGA TCC TTG CAG TAT GCT TCC-3'), Rb-2 (5'-GCT GTT AGC TAC CAT CTG ATT TAT-3'), Rb-3 (5'-ATG GTA GCT AAC AGC GAC CGT GTG-3') and Rb-7 (5'-GCG AAT TCA ATC CAT GCT ATC ATT-3'); the recombinant vector is expressed to obtain a recombinant DNA in which a nucleotide coding cysteine residue is substituted by a nucleotide coding alanine residue;

and the recombinant DNA is expressed to produce a substrate in which the cysteine reside is substituted by the alanine reside.

(ii) Labeling of the Thiophosphate Group Introduced in the Substrate and Measurement of the Amount of the Label In order to label the substrate by coupling the labeling fluorophore or the labeling enzyme with sulfur atom of the introduced thiophosphate group, a liquid of pH 7.5 to 9.0, preferably 8.5, containing 0. 1 to 1.0 mg/mL of the substrate into which the thiophosphate group is introduced is reacted with 10 to 100 equivalents of a labeling fluorophore or a labeling enzyme having a functional group which reacts with the thiol group, with respect to 1 equivalent of the substrate for 10 minutes to 2 hours. This reaction is stopped by adding a free thiol, for example, β-ME (β-mercaptoethanol), DTT (dithiothreitol) or the like.

In the case where the substrate is labeled with the labeling fluorophore, the amount of fluorescence from the labeling fluorophore is measured. The measured amount of fluorescence is compared with a reference curve which has been produced beforehand from the amount of fluorescence measured about the known amount of the substrate, and thereby the amount of the labeled substrate is calculated. The amount of the labeled substrate is regarded as an activity value of the activated CDK contained in the sample.

In the case where the substrate is labeled with the labeling enzyme, the labeling enzyme is reacted with a substance which generates an optically detectable substance by reaction with the labeling enzyme. The amount of the generated product is optically measured and the measured amount is compared with a reference curve which has been produced beforehand, and thereby the activity value of the activated CDK contained in the sample is calculated. Here the optically detectable substance means a substance whose existence can be detected by measuring fluorescence, absorbance and/or the like of the substance.

As examples of the labeling fluorophore capable of binding to the sulfur atom of the thiophosphate group, may be mentioned fluorescein, coumarin, eosin, phenanthroline, pyrene, Rhodamine and the like, among which fluorescein is preferred. In order that the labeling fluorophores binds to the sulfur atom of the thiophosphate group, the labeling fluorophores have functional groups such as an alkyl halide, maleimide, aziridine site and the like which react with the thiol group for labeling the sulfur atom of the thiophosphate group.

As examples of the labeling fluorophore having a functional group which reacts with the thiol group, may be mentioned iodoacetyl-FITC(fluorecein isothiocyanate), 5-(bromomethyl)fluorecein, fluorecein-5-maleimide, 5-iodoacetamidefluorecein (5-IAF), 6-iodoacetamidefluorecein (6-IAF), 4-bromomethyl-7-methoxycoumarin, eosin-5-iodoactamide, eosin-5-maleimide, eosin-5-iodoacetamide, N-(1,10-phenenthrolin-5-yl)bromoacetamide, 1-pyrenebutylchloride, N-(1-pyreneethyl)iodoacetamide, N-(1-pyrenemethyl)iodoacetamide (PMIA amide), 1-pyrenemethyliodoacetate(PMIA ester), Rhodamine red C2 maleimide and the like, among which iodoacetyl-FITC is preferable.

Alternatively, the labeling fluorophore may be introduced to thiophosphate group by reacting the molecule with biotin which has a functional group reacting with sulfur atom of thiophosphate group, for example, iodoacetylbiotin, and then reacting the molecule with a labeling fluorophore covalent-bound to avidin for taking advantage of the affinity of biotin to avidin.

The labeling enzyme may be introduced to sulfur atom of thiophosphate group by introducing iodoacetylbiotin to sulfur atom and then reacting the molecule with a labeling enzyme covalent-bound to avidin which has affinity to biotin. As such enzymes, may be mentioned β galactosidase, alkaline phosphatase, peroxidase and the like, among which peroxidase is preferred.

The amount of the labeled substrate may be measured by measuring the amount of fluorescence from the labeling fluorophore or by allowing a substance which generates an optically detectable product by reaction with the labeling enzyme to act on the substrate labeled with the labeling enzyme and then optically measuring the generated product.

More particularly, where the labeling fluorophore is used, the labeling fluorophore is excited by a specific wavelength and analyzed by a fluorescent image analyzer. The wavelength of applied light may vary depending upon the type of a labeling fluorophore used. For example, light of 488 nm wavelength is applied for excitation where the labeling fluorophore is fluorescein.

Where the labeling enzyme is used, a substrate which will produce a fluorophore by reaction with the labeling enzyme is added to the substrate labeled with the labeling enzyme in order to produce the fluorophore by reaction with the labeling enzyme. The produced fluorophore is excited by light having a specific wavelength and the emitted fluorescence is detected. The substrate which produces a fluorophore by reaction with the labeling enzyme may be ECL-plus in the case where the labeling enzyme is peroxidase. The substrate may be selected as appropriate depending upon a labeling enzyme used.

The amount of the labeling fluorophore or the amount of the fluorophore produced by the reaction is measured and applied to the reference curve made beforehand in order that the activity of the activated CDK is calculated. The reaction liquid of the labeled substrate needs to be diluted to such a degree that the amount of fluorescence from the labeling fluorophore or the fluorophore produced by the reaction with the labeling enzyme falls within the range of the reference curve. For example, the reaction liquid may be diluted 100 to 500 fold. As diluents, may be used TBS (50 mM Tris-HCl of pH 7.5, 150 mM NaCl), water, an aqueous sodium chloride solution and the like. In the case of aqueous sodium chloride solution, the concentration of sodium chloride may preferably be in the range of 100 to 500 mM. In the case where the reaction liquid is diluted, the dilution is taken into account when the activity of the activated CDK is calculated. The resulting activity of the activated CDK is the activity of the activated CDK in a specific amount of protein taken from the total protein of the prepared sample.

The reference curve is preferably produced beforehand using a known amount of the substrate to which thiol group is introduced. Also biotinylated actin may be used instead. Biotinylated actin is known to have the same behavior to reaction with the labeling fluorophore and the labeling enzyme as the substrate to which thiol groups has been introduced. In this case, the activity of the activated CDK is required to be calculated from the amount of biotinylated actin.

The present invention also provides a method for diagnosing cancers such as stomach cancer, colon cancer, breast cancer, lung cancer, esophageal cancer, prostate cancer, hepatic cancer, kidney cancer, bladder cancer, skin cancer, uterine cancer, cerebral tumor, osteosarcoma and myeloma, from the results of the CDK activity determined by the determination method of the present invention.

EXAMPLES

Exemplary Method 1

(Determination of Activated CDK1: Using Histone H1 as a Substrate and Utilizing Peroxidase-Labeling)

First Step:

In ice bath, HeLa cells (carcinoma cells of uterine cervix) were lysed in a lysis buffer containing 0.1 w/v % NP40 (surfactant Nonidet P-40), 50 mM Tris-HCl, pH 7.4, 5 mM EDTA, 50 mM sodium fluoride, 1 mM sodium orthovanadate and 100 μL/mL protease inhibitor cocktail (Sigma), in a proportion of $1 \times 10^7$ cells/5 mL buffer, by 10 times repeated sucking and discharging with a 5-mL syringe provided with a 23 G needle. A cell lysate was thus prepared. Insolubles were removed by centrifugation at 4° C. at 15,000 rpm for 5 minutes. The total amount of protein contained in the supernatant was measured by a DC protein kit (Bio-Rad) using bovine IgG as reference.

Second Step:

A sample was prepared by adding 10 μg of the lysed protein in the total amount to 500 μL of the lysis buffer in an Eppendorf tube of 1.5 mL volume. To the prepared sample, 10 μL of polyclonal anti-CDK antibody (Santa Cruz Biotechnology) were added. A 1:1 (sepharose beads:lysis buffer) slurry of 60 μL sepharose beads (finally 30 μL of enclosed beads) coated with Protein A was added to the resulting sample, which was incubated at 4° C. for an hour with continuous rotation. The beads were taken out of the sample and washed with 1 mL of the lysis buffer twice. Then the beads were washed once with 1 mL of a kinase buffer containing 50 mM Tris-HCl, pH 7.4, 10 mM magnesium chloride ($MgCl_2$) and 1 mM DTT. The beads were suspended again in 15 μL of the kinase buffer.

Third Step:

To the obtained suspension, 10 μL of a histone H1 solution (0.1 mg/mL solution in 50 mM Tris-HCl, pH 7.4) were added. Then 10 μL of an ATP-γS solution (10 mM aqueous solution) were added to the suspension. The resulting suspension was incubated at 37° C. for 10 minutes with continuous oscillation. The beads were precipitated by centrifugation at 10,000 rpm for 10 seconds and 30 μL of supernatant were collected. To the supernatant, were added 25 μL of a binding buffer containing 150 mM Tris-HCl and 5 mM EDTA of pH 9.2 since pH 8.5 is the optimum condition for binding reaction of iodoacetylbiotin with thiophosphoric acid. To the resulting supernatant, 20 μL of a 40 mM PEO-iodoacetylbiotin (Pierce) solution (in a 20 mM phosphate buffer of pH 6.0) were added. The supernatant was incubated in a dark place at room temperature for 90 minutes. The reaction with iodoacetylbiotin was stopped by adding 7.5 μL of β-ME (β-mercaptoethanol). The reaction liquid was diluted with TBS (50 mM Tris-HCl, pH 7.4, 150 mM sodium chloride).

Fourth Step:

The diluted reaction liquid, 50 μL, was placed and absorbed onto a PVDF membrane using a slot blotter. The membrane was washed once with 50 mL of TBS-T (a TBS solution containing 0.05 w/v % Tween 20). In order to prevent the membrane to react with avidin-peroxidase, a hydrophobic part of the membrane was blocked with BSA (bovine serum albumin) beforehand. More particularly, the membrane was blocked with 3 w/v % of BSA in TBS-T at room temperature for 30 minutes. The membrane was reacted with avidin-peroxidase (Vector) (50,000-fold diluted with TBS-T) at room temperature for 10 minutes. The membrane was washed with 50 mL of TBS-T three times. Then the membrane was reacted with ECL-plus (Amersham) for 5 minutes. A solution of ECL-plus was prepared according to the manufacturer's instructions. The reaction was stopped by washing the membrane with 200 mL of water. Bands of fluorescence were visualized by Molecular Imager (Bio-Rad) and quantified.

Exemplary Method 2

(Determination of Activated CDK1: Using Histone H1 as a Substrate and Utilizing FITC-labeling This method was carried out in the same manner as Exemplary Method 1 except that avidin-FITC was used in place of avidin-peroxidase and ECL-plus was not reacted with the membrane in the above fourth step.

Exemplary Method 3

Determination of Activated CDK2 : Using Histone H1 as a Substrate and Utilizing FITC-labeling First Step:

Tissue having a wet weight of 10 mg to 50 mg was put in a Eppendorf tube (1.5 mL volume), to which 800 μL of the lysis buffer mentioned in the first step of Exemplary Method 1 were added. The mixture was ground down with a pestle. A basic movement of the pestle turning right to left at 90° at a pressing force of 5 kg was repeated 10 times. The resulting crude liquid of solubilized cells was passed through a syringe (1 mL volume) fed with glass wool (about 0.1 g weight) and provided with a disk filter (Milipore) having a pore size of 0.45 μm at the tip thereof. Thereby was prepared a liquid of solubilized cells from which insolubles and lipid were removed. The total amount of protein contained in the supernatant was measured by a DC protein kit (Bio-Rad) using bovine IgG as reference.

Second Step:

The Second Step was carried out in the same as in the second step of Exemplary Method 1.

Third Step:

To the suspension, 10 μL of a histone H1 solution (0.1 mg/mL solution in 50 mM Tris-HCl, pH 7.4) were added. Then 10 μL of an ATP-γS solution (10 mM aqueous solution) were added to the suspension. The resulting suspension was incubated at 37° C. for 90 minutes with continuous oscillation. The beads were precipitated by centrifugation at 1,000 rpm for 10 seconds and 30 μL of supernatant were collected. To 18 μL of the supernatant, were added 15 μL of a binding buffer containing 150 mM Tris-HCl, pH 9.2 and 5 mM EDTA. To the resulting supernatant, 10 μL of a 5 mM iodoacetylfluorecein (Pierce) solution (in a 50 mM phosphate buffer of pH 6.0 and 50% dimethylsulfoxide) were added. The mixture was incubated in a dark place at room temperature for 90 minutes. The reaction of iodoacetamid-ofluorecein was stopped by adding 43 μL of β-ME. The reaction liquid was diluted 5 fold to 10 fold with TBS (50 mM Tris-HCl, pH 7.4, 150 mM sodium chloride).

Fourth Step:

The diluted reaction liquid, 50 μL, was placed and absorbed onto a PVDF membrane using a slot blotter. The membrane was washed with 50 mM TBS-T (a TBS solution containing 0.05 w/v % Tween 20) for 10 minutes three times with oscillation. Thereafter the membrane was washed with 200 mL of water and dried. Bands of fluorescence were visualized by Molecular Imager (Bio-Rad) and quantified by an image analyzer.

Exemplary Method 4

Determination of Activated CDK2: Using Histone H1 as a Substrate and Utilizing FITC-labeling First Step:

This step was carried out in a manner similar to the first step of Exemplary Method 1 using K562 cell line.

Second Step:

Samples were prepared in graded concentrations of 0, 25, 50, 100 and 200 µg/mL of the total amount of protein of solubilized K562 cells in 500 L of the lysis buffer and put in Eppendorf tubes. To each of the samples, 10 µL of polyclonal anti-CDK antibody (200 µg/mL, Santa Cruz Biotechnology) were added. To the resulting samples, a 1:1 (sepharose beads:lysis buffer) slurry of 40 µL sepharose beads coated with Protein A was added. The samples were incubated at 4° C. for an hour with continuous rotation. The beads were taken out of the samples and washed with 1 mL of the lysis buffer twice. Then the beads were washed once with 100 mM Tris-HCl of pH 7.4 and 100 mM sodium chloride and further with 100 mM Tris-HCl of pH 7.4.

Third Step:

To the beads, 50 µL of kinase buffer solution containing histone H1 (40 mM Tris-HCl, pH7.4, 18 mM magnesium chloride, 2 mM ATP-γS, 6 µg/test histone H1) were added. The resulting suspension was incubated at 37° C. for 90 minutes with continuous oscillation. The beads were precipitated by centrifugation at 1,000 rpm for 10 seconds and 36 µL of supernatant were collected. To 36 µL of the supernatant, were added 30 µL of a binding buffer containing 150 mM Tris-HCl and 2.5 mM EDTA of pH 9.2. Further, 20 µL of a 35 mM PEO-iodoacetylbiotin (Pierce) solution (in a 50 mM phosphate buffer of pH 6.0) were added. The resulting mixture was incubated in a dark place at room temperature for 90 minutes. The reaction was stopped by adding an equivalent amount (86 µL) of β-ME. The reaction liquid was diluted 5 fold to 10 fold with TBS (50 mM Tris-HCl, pH 7.4, 150 mM sodium chloride).

Fourth Step:

The diluted reaction liquid, 50 µL, was placed and absorbed onto a PVDF membrane using a slot blotter. The obtained membrane was blocked with 1 w/v % BSA for 30 minutes and washed with TBS for 5 minutes. Reaction was conducted in a solution of avidin-FITC (Pierce) (500-fold diluted with TBS) at 37° C. for 60 minutes. After the reaction, the membrane was washed with TBS three times and with water once, and dried. Bands of fluorescence were visualized by Molecular Imager (Bio-Rad) and measured.

Production Example 1

Production of a Recombinant Vector Coding for a Rb (Retinoblastoma Protein) whose Cysteine Residue is Substituted by Alanine Residue and a Protein Produced by Expression of the Vector.

(1) Construction of Expression Vector

First a cDNA coding human Rb was cloned from a cDNA library (Stratagene) of human placenta.

For constructing a plasmid for expressing a C-terminal (from Leu 769 to Lys 928) of human Rb whose Cys 853 was uniquely modified to Ala, a two-stage PCR was carried out using oligonucleotide primer with pJ3Ω vector containing the full length of cDNA of human Rb.

1. First PCR

First, for amplifying a region of human Rb protein corresponding to Leu769 to Asp921 and substituting Cys 853 by Ala at the same time, the two-stage PCR was carried out using four species of primers. The primers used were primer Rb-1 (5'-ACA GGATCC TTG CAG TAT GCT TCC-3', into which a BamHI site (as underlined) was introduced) and Rb-7 (5'-GCGAATTCA ATC CAT GCT ATC ATT-3', into which a EcoRI site (as underlined) was introduced), which were primers at both ends, a primer Rb-2 whose 853 position was changed into Ala codon (AGC) (5'-GCT GTT AGC TAC CAT CTG ATT TAT-3', the point modified codon is shown as underlined) and its complementary primer Rb-3 (5'-ATG GTA GCT AAC AGC GAC CGT GTG-3'). The PCR was carried out with a primer set of Rb-1/Rb-2 and a primer set of Rb-3/Rb-7 using the total length of cDNA of human Rb as a template under the following reaction conditions, to obtain PCR fragments 1 and 2, which were complementary in regions corresponding to the primer Rb-2 and the primer Rb-3.

Composition of Reaction Liquid (for Fragment 1 Corresponding to Nucleotide 2305 to 2565)

| | |
|---|---|
| PJ3 Ω-Rb | 250 ng |
| Taq DNA polymerase (TaKaRa Ex Taq, Takara Shuzo) | 0.03 U |
| Buffer for TaKaRa Ex Taq (Takara Shuzo) | |
| MgCl$_2$ (Takara Shuzo) | 2 mM |
| dNTPs (Takara Shuzo) | 250 µM |
| Primer Rb-1 | 1 µM |
| Primer Rb-2 | 1 µM |
| Total | 50 µL |

Composition of Reaction Liquid (for Fragment 2 Corresponding to Nucleotide 2551 to 2763)

| | |
|---|---|
| PJ3 Ω-Rb | 250 ng |
| Taq DNA polymerase (TaKaRa Ex Taq, Takara Shuzo) | 0.03 U |
| Buffer for TaKaRa Ex Taq (Takara Shuzo) | |
| MgCl$_2$ (Takara Shuzo) | 2 mM |
| dNTPs (Takara Shuzo) | 250 µM |
| Primer Rb-3 | 1 µM |
| Primer Rb-7 | 1 µM |
| Total | 50 µL |

Reaction Temperature

At 95° C. for 5 minutes

At 94° C. for 30 seconds, at 55° C. for 1 minute, at 72° C. for 1 minute (15 cycles)

At 72° C. for 2 minutes

2. Treatment of Overhang

A-3' overhangs of the PCR products were treated with Klenow under the following conditions.

Composition of Reaction Liquids

| | |
|---|---|
| PCR fragment 1 and 2 | |
| Klenow fragment (Takara Shuzo) | 0.07 U |
| Buffer for Klenow fragment (Takara Shuzo) | |
| dNTPs (Takara Shuzo) | 250 µM |

Reaction Temperature
At 37° C. for 1 hour

3. Second PCR

Thereafter, using a mixture of the PCR products as a template, PCR was carried out with a primer set of Rb-1/Rb-7 at both ends under the following reaction conditions, to amplify a DNA fragment of 470 bp corresponding to Leu769 to Asp921 in which Cys 853 was substituted by Ala.

Composition of Reaction Liquid
Klenow-treated PCR fragment 1 and 2

| | |
|---|---|
| Taq DNA polymerase (TaKaRa Ex Taq, Takara Shuzo) | 0.03 U |
| Buffer for TaKaRa Ex Taq (Takara Shuzo) | |
| MgCl$_2$ (Takara Shuzo) | 2 mM |
| dNTPs (Takara Shuzo) | 250 μM |
| Primer Rb-1 | 1 μM |
| Primer Rb-7 | 1 μM |
| Total | 50 μL |

Reaction Temperature
At 95° C. for 5 minutes
At 94° C. for 30 seconds, at 55° C. for 1 minute, at 72° C. for 1 minute (15 cycles)
At 72° C. for 2 minutes 4. Cloning into pMe1BacA In order to express a Rb protein having a secretion signal added at the N terminal, after the DNA fragment of 470 bp amplified in the previous step 3 was digested with BamHI and EcoRI, the digested fragment was inserted at the BamHI site and at the EcoRI site of pMe1BacA (Invitrogen). The obtained plasmid was referred to as pMe1BacA-Rb.

5. PCR

Using the obtained plasmid as a template, PCR was carried out using primer Rb-9 (5'-GC<u>GAATTC</u>A TGA AAT TCT TAG TCA-3', into which the EcoRI site was introduced as underlined) and primer Rb-5 (5'-GTT <u>CTCGAG</u> TCA ATC CAT GCT ATC ATT-3', into which the XhoI site was introduced as underlined) under the following conditions, to amplify the DNA fragment of 540 bp to which the secretion signal was added.

Composition of Reaction Liquid

| | |
|---|---|
| pMelBacA-Rb | 250 ng |
| Taq DNA polymerase (TaKaRa Ex Taq, Takara Shuzo) | 0.03 U |
| Buffer for TaKaRa Ex Taq (Takara Shuzo) | |
| MgCl$_2$ (Takara Shuzo) | 2 mM |
| dNTPs (Takara Shuzo) | 250 μM |
| Primer Rb-9 | 1 μM |
| Primer Rb-5 | 1 μM |
| Total | 50 μL |

Reaction Temperature
At 94° C. for 5 minutes
At 94° C. for 30 seconds, at 55° C. for 1 minute, at 72° C. for 1 minute (25 cycles)
At 72° C. for 2 minutes 6. Cloning into pFastBac1

The DNA fragment of 540 bp containing the secretion signal amplified in the previous step 5 was digested with EcoRI and XhoI, and then was inserted at the EcoRI site and at the XhoI site of pFastBac1 (Lifetech).

(2) Isolation of Recombinant Virus by Bac-To-Bac Baculovirus Expression System (Lifetech)

The expression plasmid obtained in the previous step 6 was used for isolating a recombinant virus, that is, according to the manufacturer's instructed protocol.

(3) Expression

The liquid of the recombinant virus prepared in the previous step (2) was infected to insect cells (High Five Cell, Invitroge) under the condition of MOI=10 to express a region corresponding to Leu 769 to Asp 921 containing Cys 853 substituted by Ala. The secretion of the expressed protein into a medium (CELL405, JRH Biosciences) was confirmed by Western blotting using an anti-human Rb polyclonal antibody (Rb(C-15), Santa Cruz), and the medium was harvested five days after the infection.

(4) Purification of Expressed Protein

The medium containing the Rb recombinant protein obtained in the previous step (3) was exchanged with 50 mM MES buffer (pH 6.0) by PD-10 column (Pharmacia), and then the protein is eluted by CM-5pW column (Tosoh) using a linear gradient of 0 to 1 M NaCl. The elution of the Rb recombinant protein at about 0.3 M NaCl was confirmed by Western blotting using an anti-human Rb polyclonal antibody (Rb(C-15), Santa Cruz).

The obtained protein was used in place of histone H1 as a substrate in the third step of Exemplary Method 1 for determination of CDK4 or CDK6.

Exemplary Method 5

Determination of Activated CDK4: Utilizing the Recombinant Human Rb Produced in Production Example 1 as a substrate and FITC-Labeling First Step:

This step was carried out in the same manner as in the first step of Examplary Method 3.

Second Step:

Samples were prepared by placing the solubilized K562 cells and the lysis buffer into Eppendorf tubes of 1.5 mL volume so that 0, 50, 100, 125 and 250 μg of the total amount of protein were in 500 μL of the lysis buffer. To each of the samples, 10 μL of a polyclonal anti-CDK 4 antibody (200 μg/mL Santa Cruz Biotechnology) were added. A 1:1 (sepharose beads:lysis buffer) slurry of 40 μL sepharose beads coated with Protein A was added to the resulting samples, which were incubated at 4° C. for an hour with continuous rotation. The beads were taken out of the samples and washed with 1 mL of the lysis buffer twice. Then the beads were washed once with 100 mM Tris-HCl of pH 7.4 and 100 mM sodium chloride and further washed once with 100 mM Tris-HCl of pH 7.4.

Third Step:

To the obtained beads, 50 μL of phosphorylation solution containing the recombinant human Rb protein produced in Production Example 1 (40 mM Tris-HCl, pH 7.4, 200 mM magnesium chloride, 3.3 mM ATP-γS, 20 μL recombinant human Rb protein solution:50 mM MES buffer, pH 6.0) were added. The resulting suspension was incubated at 37° C. for 90 minutes with continuous oscillation. The beads were precipitated by centrifugation at 1,000 rpm for 10 seconds and 36 μL of supernatant were collected. To 36 μL of the supernatant, were added 30 μL of a binding buffer containing 150 mM Tris-HCl and 2.5 mM EDTA of pH 9.2.

To the resulting supernatant, 20 μL of a 50 mM PEO-iodoacetylbiotin (Pierce) solution (in a 50 mM phosphate buffer, pH 6.0). The supernatant was incubated in a dark place at room temperature for 90 minutes. Thereafter, the supernatant was treated with an equivalent amount (86 μL) of an SDS-sample loading buffer (0.125 M tris-HCl, pH6.8, 4% SDS, 10% β-ME, 25% glycerine, bromophenol blue) at 100° C. for 5 minutes.

Fourth Step:

The samples prepared in the third step was subjected to SDS-PAGE under the condition of 20 μL/lane (pre-cast gel, 4–20% gradient, 10 mm×10 mm, Daiichi Kagaku Yakuhin). The conditions of the SDS-PAGE were in compliance with the instruction protocol of Daiichi Kagaku Yakuhin (60 mA, 40 minutes). After the SDS-PAGE, the protein extended in the gel was electrically transferred to a PVDF membrane (10V, 30 minutes, Western blotting). The obtained membrane was blocked with 4 w/v % BSA for 30 minutes and washed with TBS-T for 5 minutes. Subsequently, the membrane was reacted in a solution of avidin FITC (Pierce) (diluted 1,000 fold with TBS-T) at 37° C. for 30 minutes. After reaction, the membrane was washed with TBT-T twice and with water once, and dried. Bands of fluorescence were visualized by Molecular Imager (Bio-Rad) and measured.

Determination of Activity of Activated CDK1

Figure 1:
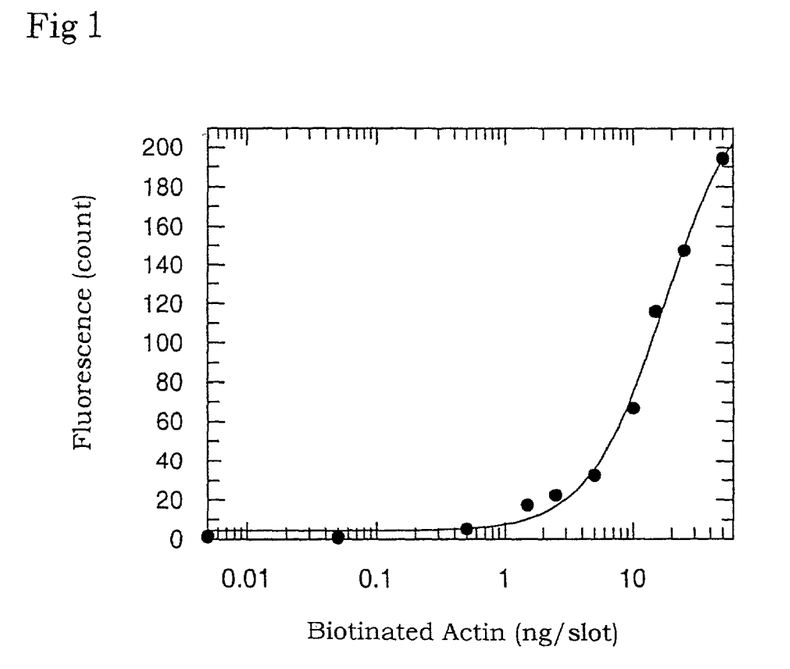
FIG. 1 shows a reference curve representing a relation between the amount (ng/slot) of biotinated actin and the amount of fluorescence (count) obtained in Example 1.

1. Production of Reference Curve Using Biotinyted Actin (BA) as Reference Substance Samples of BA are prepared in graded concentrations from 0 to 1000 ng/mL and each of the samples, 50 mL, is put into a slot. The sample in the slot is treated as in the fourth step of Exemplary Method 1. Since BA is labeled with peroxidase, BA produces a fluorophore from ECL-plus (fluorescent substrate) in the fourth step. The amount of fluorescence is measured for the fluorophores generated in the samples containing the graded concentrations of BA and is indicated by count (CNT) values. The obtained data are plotted with the BA concentration in abscissa and the CNT value in ordinate, and a reference curve is produced under the reaction conditions of Exemplary Method 1. FIG. 1 shows the obtained reference curve.

Figure 2:
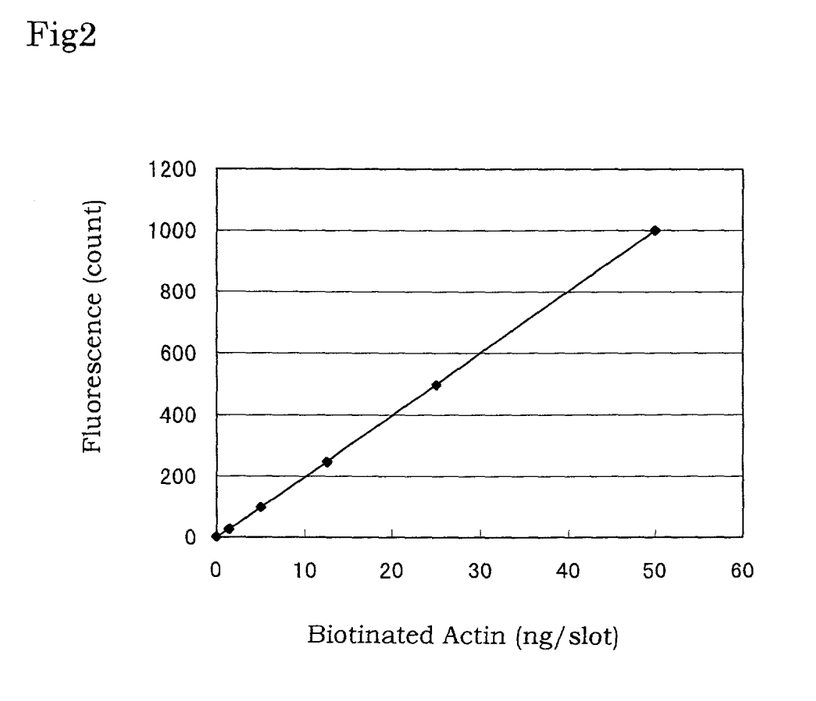
FIG. 2 shows a reference curve representing a relation between the amount (ng/slot) of biotinated actin and the amount of fluorescence (count) obtained in Example 2.

In the same manner, the samples in the slots are treated as in the fourth step of Exemplary Method 1, and a reference curve is produced in the above-described manner under the reaction conditions of Exemplary Method 2. FIG. 2 shows the obtained reference curve.

2. Calculation of Activity of Activated CDK1

With regard to Exemplary Methods 1 and 2, blank samples are prepared which are treated according to Exemplary Method 1 except that the anti-CDK antibody is not added. The amount of fluorescence from the blank samples is measured. The obtained CNT values are converted to BA concentrations using the reference curves produced for Exemplary Methods A and B as described above. The activity of the activated CDK is calculated by substituting the obtained BA concentrations into the following formula:

{(the converted BA concentration of a sample)−(the converted BA concentration of the blank sample)}×(the dilution ratio of the sample)=(the activity of the activated CDK1)  Formula 1

If the produced reference curve is not a sigmoid curve but a linear line (e.g., Exemplary Method 2), the activity of the activated CDK may be calculated by calculating (the CNT value of a sample)−(the CNT value of the blank sample), converting the obtained remainder to BA concentration using the reference curve and substituting the converted BA concentration into the following formula:

(the converted BA concentration of the remainder of the CNT value of the sample minus the CNT value of the blank sample)×(the dilution ratio of the sample)=(the activity of the activated CDK)  Formula 2

Example 1

(Measurement of Activity of Activated CDK1 of Sample Treated According to Exemplary Method 1)

The amount of fluorescent of 450-fold diluted samples prepared by Exemplary Method 1 using the anti-CDK1 antibody was measured as described above. Sample 1 was prepared using HeLa cells in a growth phase and Sample 2 was prepared using HeLa cells in a stationary phase. Since the reference curve was a sigmoid curve as shown in FIG. 1, the activity of the activated CDK1 was calculated using Formula 1, that is, by producing blank samples as described above, measuring the amount of fluorescence of the blank samples and substituting the CNT values of the blank samples and the samples into Formula 1. The results are shown in Table 2.

TABLE 2

|  | CNT value | Activity of activated CDK1 (ng/slot) |
| --- | --- | --- |
| Sample 1 | 147.6 | 6921.4 |
| Blank of Sample 1 | 68.7 | — |
| Sample 2 | 133.3 | 5121.85 |
| Blank of Sample 2 | 69.1 | — |

Example 2

(Determination of Activity of Activated CDK1 of Sample Treated According to Exemplary Method 2)

The amount of fluorescent of 100-fold diluted samples prepared by Exemplary Method 2 using the anti-CDK1 antibody was measured as described above. Since the reference curve was linear as shown in FIG. 2, it was found that the activity of the activated CDK1 was able to be calculated using any one of Formula 1 and Formula 2.

Determination of Activity of Activated CDK2

Example 3

(Determination of Activity of Activated CDK2 of Samples Treated by Exemplary Method 3)

Figure 3:
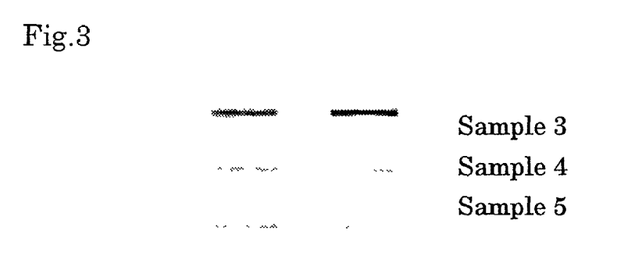
FIG. 3 shows a fluorescent band obtained in Example 3.

Sample 3 was prepared using the anti-CDK2 antibody according to Exemplary Method 3. As controls, Sample 4 was prepared according to Exemplary Method 3 without using the anti-CDK2 antibody, and Sample 5 was prepared according to Exemplary Method 3 except that a non-specific IgG antibody was used instead of the anti-CDK2 antibody in the second step. The fluorescence bands of Samples 3 to 5 are shown in FIG. 3. The amount of fluorescence of the bands were numerically represented by Molecular Imager (Bio-Rad). The obtained amount of fluorescence is shown in Table 3.

TABLE 3

| | CNT value |
|---|---|
| Sample 3 | 363 |
| Sample 4 | 198 |
| Sample 5 | 192 |

The above results show that a non-specific reaction was not observed in the case where the non-specific IgG antibody was added instead of the anti-CDK2 antibody (Sample 5) and therefore that the activity of the activated CDK2 was able to be determined by the method of the present invention.

Example 4

(Determination of Activity of Activated CDK2 of Sample Treated by Exemplary Method 4)

Figure 4:
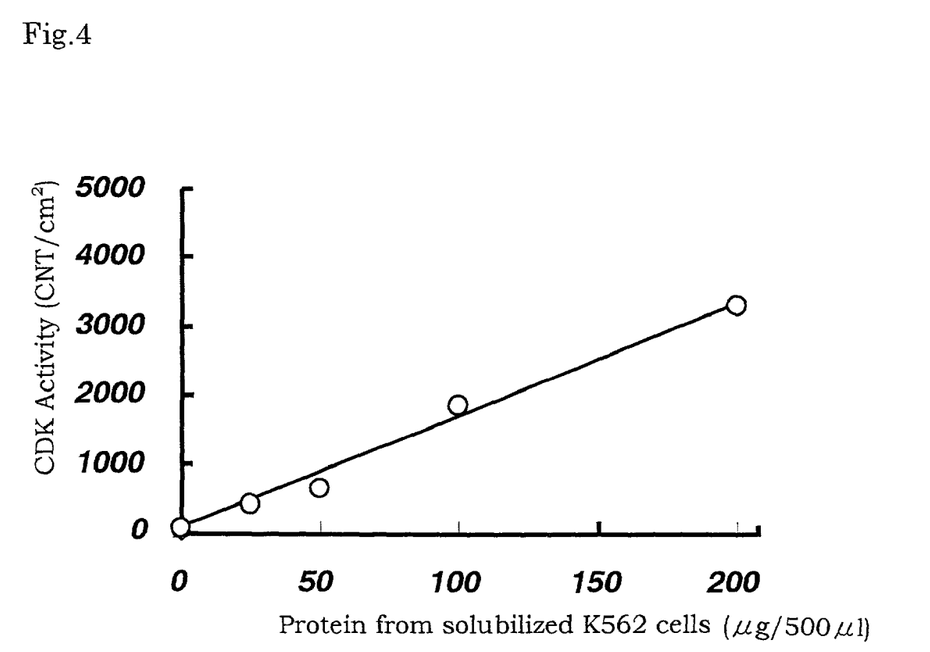
FIG. 4 shows a reference curve for measuring the activated CDK2.

1. Production of Reference Curve Using K562 Cell Line (Premyelocytic Leukemia) as Reference Substance The amount of fluorescence was measured about samples having graded concentrations of 0 to 200 µg/mL produced according to Exemplary Method 4 and represented by CNT values. The obtained data were plotted with the concentration of K562 cell line in abscissa and the CNT value in ordinate to produce a reference curve. The obtained reference curve is shown in FIG. 4.

2. Calculation of Activity of Activated CDK2

A specimen was prepared according to Exemplary Method 4 except that an unknown sample was used instead of the sample of solubilized K562 cells. The amount of fluorescence of the specimen was measured, and the obtained CNT value was converted to a CDK2 activity of the solubilized K562 cells using the above-produced reference curve to calculate the activity.

Determination of Activity of Activated CDK4

Example 5

(Determination of Activity of Activated CDK4 of Samples Treated by Exemplary Method 5)

Figure 5:
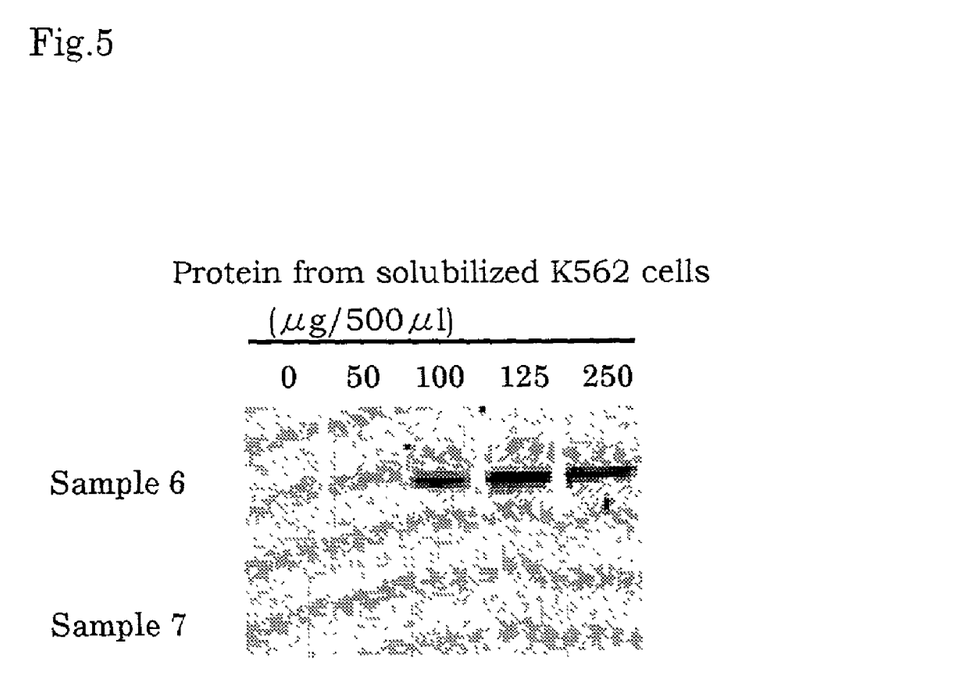
FIG. 5 shows a fluorescent band obtained in Example 5.

Sample 6 was prepared according to Exemplary Method 5 using the anti-CDK4 antibody. As a control, Sample 7 was prepared according to Exemplary Method 5 except that the anti-CDK4 antibody was not used. The bands of fluorescence of Samples 6 and 7 are shown in FIG. 5.

Example to Prove the Specificity of Activated CDK2 Measurements to Activity of CDK2 Using CDK-specific Inhibitor Example 6

(In the Case of Activated CDK2)

First Step:

This step was carried out in the same manner as in the first step of the Exemplary Method 1 using K562 cell line (premyelocytic leukemia).

Second Step:

A sample was prepared by placing the solubilized K562 cells and the lysis buffer into an Eppendorf tube of 1.5 mL volume so that 250 µg of the total amount of protein of the solubilized K562 cells were in 500 µL of the lysis buffer. To the sample, 10 µL of a polyclonal anti-CDK2 antibody (200 µg/mL, Santa Cruz Biotechnology) were added. A 1:1 (sepharose beads:lysis buffer) slurry of 40 µL sepharose beads coated with Protein A was added to the resulting sample, which was incubated at 4° C. for an hour with continuous rotation. The beads were taken out of the sample and washed with 1 mL of the lysis buffer twice. Then the beads were washed once with 100 mM Tris-HCl of pH 7.4 and 100 mM sodium chloride and further washed once with 100 mM Tris-HCl of pH 7.4.

Third Step:

As CDK inhibitors, were used Butyrolactone I (Calbiochem) which were inhibitors to CDK1 and CDK2 and Staurosporine (Calbiochem) which had a broad inhibition spectrum including inhibition to CDK2. Phosphorylation solutions (40 mM Tris-HCl, pH 7.4, 18 mM magnesium chloride, 2 mM ATP-γS, 6 µ/test histone H1 ), 50 µL, containing histone H1 and the CDK inhibitors (final concentrations of 0, 1, 10, 30, 100 µM of Butyrolactone, or final concentrations of 0, 0.3, 1, 10, 30 µM of Staurosporine) were added to the beads. The resulting suspensions were incubated at 37° C. for 90 minutes with continuous oscillation. The beads were precipitated by centrifugation at 1,000 rpm for 10 seconds, and 36 µL of supernatant was collected. To 36 µL of the supernatant, 30 µL of a binding buffer containing 150 mM Tris-HCl and 5 mM of EDTA of pH 9.2 was added. Further, 20 µL of 50 mM PEO-iodoacetylbiotin (Pierce) solution (50 mM phosphate buffer, pH 6.0) was added and the resulting mixture was incubated in a dark place at room temperature for 90 minutes. Thereafter, the mixture was treated with an equivalent amount (86 µL) of an SDS-sample loading buffer (0.125 M tris-HCl, pH6.8, 4% SDS, 10% β-ME, 25% glycerine, bromophenol blue) at 100° C. for 5 minutes.

Fourth Step:

The samples prepared in the third step was subjected to SDS-PAGE under the condition of 20 µg L/lane (pre-cast gel, 4–20% gradient, 10 mm×10 mm, Daiichi Kagaku Yakuhin). The conditions of the SDS-PAGE were in compliance with the instructions of Daiichi Kagaku Yakuhin (60 mA, 40 minutes). After the SDS-PAGE, the protein extended in the gel was electrically transferred to a PVDF membrane (10V, 30 minutes, Western blotting). The obtained membrane was blocked with a 4 w/v % BSA for 30 minutes and washed with TBS-T for 5 minutes. Subsequently, the membrane was reacted in a solution of avidin FITC (Pierce) (diluted 1,000 fold with TBS-T) at 37° C. for 30 minutes. After reaction, the membrane was washed with TBS-T twice and with water once, and dried. Bands of fluorescence were visualized by Molecular Imager (Bio-Rad) and measured.

Figure 6:
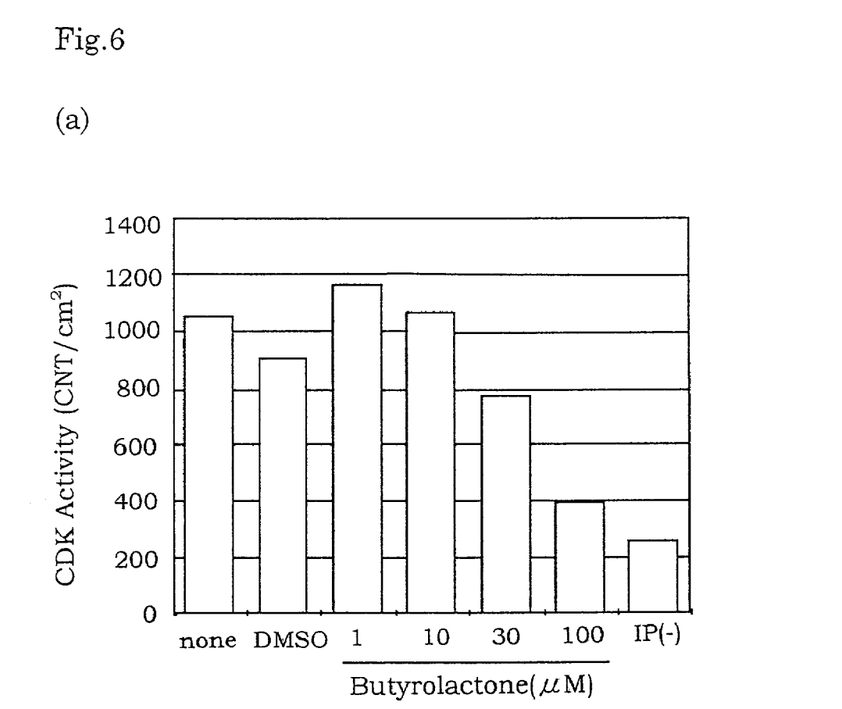
FIG. 6 is a graphical representation obtained in Example 6.

The visualized bands of fluorescence were numerically and graphically represented by an image analyzer. The results are shown in FIG. 6, wherein none represents the result of the above step without addition of the CDK inhibitors, DMSO represents the result of the above step with addition only of a solvent (dimethylsulfoxide) for the CDK inhibitors and IP (−) represents the result of the above step without addition of the CDK2 antibody. As shown in FIG. 6, the activity of CDK2 was inhibited dependently upon the amounts of the inhibitors. The results shows that the determined activity was specific to CDK2.

As shown above, the method of the present invention can measure the activity of cell cycle controlling factors accurately without using radioisotopes.

What is claimed is:

1. A method for calculating activity of a cyclin-dependent kinase in a sample prepared from a living cell comprising the steps of:
   catching the cyclin-dependent kinase in the sample by anti-cyclin-dependent kinase antibody;
   reacting an adenosine 5'-O-(3-thiotriphosphate) (ATP-γS) with a substrate for the cyclin-dependent kinase in presence of the cyclin-dependent kinase in order to introduce a monothiophosphate group into a serine or threonine residue of the substrate, the substrate not containing a sulfur atom;
   coupling a labeling fluorophore or a labeling enzyme with a sulfur atom of the introduced monothiophosphate group of the substrate in buffer solution;
   adding a thiol to the buffer solution to stop the coupling between the sulfur atom and the labeling fluorophore or the labeling enzyme;
   measuring an amount of fluorescence from the labeling fluorophore, or reacting the labeling enzyme with a substance to generate an optically detectable product and measuring an amount of the generated product; and
   calculating the activity of the cyclin-dependent kinase from the measured amount of fluorescence or the measured amount of the generated product with reference to a pre-produced reference curve.

2. The method according to claim 1, wherein the cyclin-dependent kinase is selected from the group consisting of CDK1, CDK2, CDK4 and CDK6.

3. The method according to claim 1, wherein the labeling fluorophore is a fluorescent dye.

4. The method according to claim 3, wherein the fluorescent dye is FITC.

5. The method according to claim 1, wherein the labeling enzyme is peroxidase.

6. The method according to claim 1, wherein the cyclin-dependent kinase is CDK1 or CDK2 and the substrate is histone H1.

7. The method according to claim 1, wherein the cyclin-dependent kinase is CDK4 or CDK6 and the substrate is Rb whose cysteine residue is substituted by alanine.

8. The meted according to claim 1 further comprising the step of placing the reacted substrate on a membrane, wherein the membrane comprises a hydrophobic part.

9. The method according to claim 1, wherein the thiol is at least one selected from the group consisting of a β-mercaptoethanol and a dithiothreitol.

* * * * *